United States Patent [19]

Omura et al.

[11] Patent Number: 4,525,493
[45] Date of Patent: Jun. 25, 1985

[54] HIGHLY WATER-RESISTANT ADHESIVE

[75] Inventors: Ikuo Omura; Junichi Yamauchi, both of Kurashiki, Japan

[73] Assignee: Kuraray Co., Ltd., Kurashiki, Japan

[21] Appl. No.: 573,618

[22] Filed: Jan. 25, 1984

[30] Foreign Application Priority Data

Jan. 31, 1983 [JP] Japan ................... 58-15072

[51] Int. Cl.³ .................. A61K 6/02; C08F 4/34; C08F 130/02; C09K 3/00
[52] U.S. Cl. .................... 523/116; 106/35; 433/224; 433/226; 433/228; 523/115; 523/118; 524/547; 526/276; 526/277
[58] Field of Search .................. 106/35; 526/276, 277; 523/115, 116, 118; 433/224, 226, 228; 524/547

[56] References Cited

U.S. PATENT DOCUMENTS

| | | | |
|---|---|---|---|
| 4,044,044 | 8/1977 | Saito | 526/278 |
| 4,222,780 | 9/1980 | Shibatani et al. | 106/35 |
| 4,259,075 | 3/1981 | Yamauchi et al. | 106/35 |
| 4,259,117 | 3/1981 | Yamauchi et al. | 106/35 |
| 4,322,509 | 3/1982 | Zalucha | 526/278 |
| 4,368,043 | 1/1983 | Yamauchi et al. | 106/35 |

OTHER PUBLICATIONS

European Search Report of Application No. 84 30 0528.
*Patents Abstracts of Japan*, vol. 6, No. 231(C-135)(1109), Nov. 17, 1982.
*Patent Abstracts of Japan*, vol. 7, No. 7(C-144)(1152), Jan. 12, 1983.

*Primary Examiner*—Ronald W. Griffin
*Attorney, Agent, or Firm*—Oblon, Fisher, Spivak, McClelland & Maier

[57] ABSTRACT

An adhesive which comprises (a) 1 part by weight of a compound represented by the formula

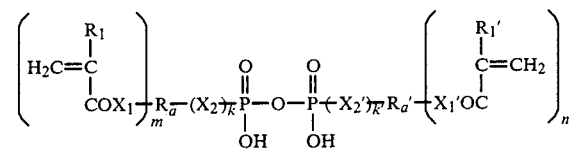

(where
$R_1$ and $R_1'$ denote H or a methyl group,
$X_1$, $X_1'$, $X_2$, and $X_2'$ denote O, S, or $NR_\alpha$ [where $R_\alpha$ is H or a $C_{1-6}$ alkyl group],
m is an integer of 1 to 4,
n is an integer of 0 to 4,
k and k' are 0 or 1,
$R_a$ is a $C_{8-40}$ organic residue having a valence of (m+1), and
$R_a'$ is a $C_{1-40}$ organic residue having a valence of (n+1)), and (b) 0 to 199 parts by weight of a monomer which is copolymerizable with said compound (a).

This adhesive firmly adheres to hard tissues of the living body such as teeth and bones, metallic materials, organic polymeric materials, and ceramics. It keeps the high adhesive strength for a long period of time under wet conditions. This adhesive is particularly useful in dentistry.

23 Claims, No Drawings

HIGHLY WATER-RESISTANT ADHESIVE

BACKGROUND OF THE INVENTION

1. Field of the Invention

This invention relates to a highly water-resistant adhesive which firmly adheres to hard tissues of the living body such as teeth and bones, metallic materials, organic polymeric materials, and ceramics. The "adhesive" as used herein not only denotes compositions used to bond adherends to one another but also encompasses compositions which are used to form a highly adhesive coating layer on the surface of adherends such as metallic materials and organic polymeric materials or used to form a highly adhesive filling material for repairing hard tissues of the living body. In other words, by "adhesive" is meant any and all compositions which are applicable for adhesion to a variety of substances including hard tissues of the living body, metallic materials, organic polymeric materials, and ceramics.

2. Description of the Prior Art

A variety of metallic materials, organic polymeric materials, and ceramic materials are in use as restorative dental materials. When in use, these materials are required to firmly adhere to teeth and/or to one another. Moreover, they are required to exhibit adhesion under the wet conditions of the mouth.

Heretofore, many attempts have been made to use a phosphoric ester compound as an adhesive in the dentistry. For example, U.S. Pat. Nos. 4,259,075, 4,259,117, and 4,368,043 disclose that a polymerizable composition containing a vinyl compound having a group of the formula

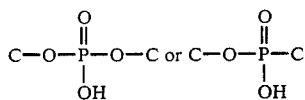

is useful as a dental adhesive. U.S. Pat. No. 4,222,780 also teaches that a polymerizable composition containing a vinyl compound having a group of the formula

is useful as a dental adhesive. In fact, some of the compositions defined in these patents have found practical use as a primer to be applied to the wall of a tooth cavity, prior to filling thereof. The compositions disclosed in the above-mentioned patents, however, have the drawback that they do not firmly adhere to a tooth unless the surface of the tooth cavity previously undergoes acid etching. In addition, they do not firmly adhere to an Ni—Cr alloy which is a common dental metallic material.

Attempts have also been made to prepare a dental adhesive from a polymerizable phosphoric ester compound as mentioned below.

(i) U.S. Pat. No. 3,882,600 discloses phosphoryl monofluoride.

(ii) There are shown $CH_2=CH-PO(OH)_2$ and $CH_2=CHC_6H_4CH_2P-O(OH)_2$ in the Journal of Dental Research, Vol. 53, p. 878–888 and Vol. 56, p. 943–952; Chemical Abstract, Vol. 77, p. 290 (66175g); and Japanese Patent Laid-open No. 44152/1976.

(iii) Japanese Patent Laid-open No. 113843/53 discloses a compound of the formula

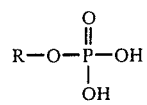

(where R is an organic residue having at least one vinyl group), with one of the two OH groups being neutralized. Said patent exemplifies the following compounds, in which M denotes a metal.

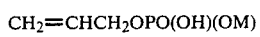

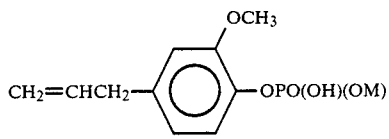

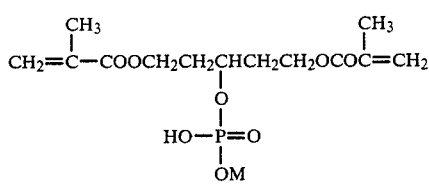

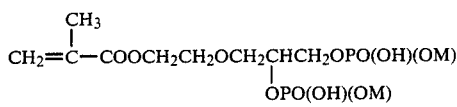

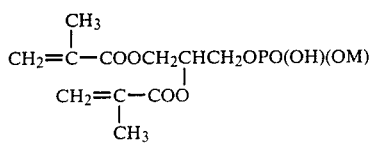

(iv) Japanese Patent Publication No. 49557/1982 discloses methacryloyloxyethane-1,1-diphosphonic acid of the formula

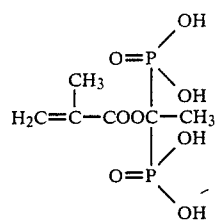

All of the compounds set forth above do not exhibit high adhesive strength (particularly to a metal) when used under a wet condition.

Japanese Patent Laid-open Nos. 131799/1982 and 164171/1982 disclose as a component of dental adhesive a pyrophosphate derivative having a polymerizable functional group and a group of the formula

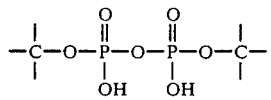

or preferably a pyrophosphate derivative of the formula

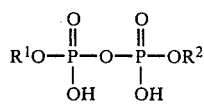

where $R^1$ denotes an allyl, methacryloyloxy (lower) alkyl, or dimethacryloyloxy (lower) alkyl; and $R^2$ denotes an allyl, methacryloyloxy (lower) alkyl or aryl; the (lower) alkyl in $R^1$ and $R^2$ may be substituted with a hydroxyl group; the lower alkyl has 6 or less carbon atoms. The patents claim that the compound increases the adhesive force for the enamel of human teeth. However, they do not mention anything about the adhesion to metals. In fact, the inventors' follow-up study showed that the compound does not significantly increase the water resistance of their adhesive strength where attached to metals.

In the industrial field, many attempts have been made to use a phosphoric ester compound as an adhesive. For example, such compounds are proposed as adhesives in U.S. Pat. Nos. 3,754,972, 3,884,864, 3,987,127, 4,001,150, 4,044,044, and 4,223,115; Japanese Patent Laid-open Nos. 20238/1974, 100596/1975, 125182/1976, 12995/1978, 11920/1981, and 44638/1982; and Japanese Patent Publication Nos. 4126/1980 and 4790/1980. However, the phosphoric ester compounds described in these patents are not necessarily satisfactory in terms of the water resistance of their adhesive strength.

SUMMARY OF THE INVENTION

This invention provides an adhesive composition useful for firmly bonding hard tissues of the living body to one another or to restorative materials (e.g., metallic, organic polymeric, and ceramic materials), or for filling the cavity of a hard tissue of the living body for restoration thereof.

This invention also provides an adhesive composition for industrial and home use for bonding metallic materials to each other or to an organic polymeric material or to a ceramic material; or bonding a ceramic material to the other ceramic material or to an organic polymeric material, and to provide an adhesive composition to be used as a coating material and paint that forms a highly adhesive film on the surface of a metallic material or ceramic material.

This invention also provides a dental adhesive to be applied to the surface of a tooth cavity prior to the filling of the cavity in order to promote firm adhesion between the tooth and the filling material.

This invention also provides a dental filling composition which firmly adheres to the tooth when used for restoring the tooth cavity.

This invention also provides a dental adhesive for bonding a dental restorative material (e.g., inlay, onlay, abutment, post, bridge, splint, orthodontic bracket, and crown) to teeth, and for bonding dental restorative materials to each other (e.g., bonding abutment to crown).

This invention provides in addition a dental adhesive to be used as a pit and fissure sealant which is applied to the tooth surface to prevent tooth decay.

This invention also provides a method for performing complete restoration of teeth by firmly bonding a filling material to a tooth and by firmly bonding restorative materials to each other, and a method for coating the tooth surface for the prevention of tooth decay.

The above-mentioned objectives of this invention are achieved by an adhesive which comprises (a) 1 part by weight of a compound represented by the formula

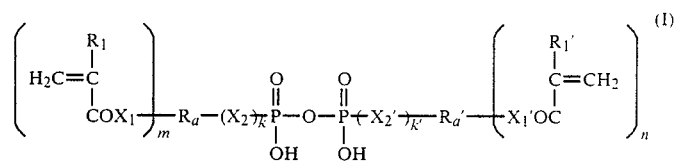

(where
$R_1$ and $R_1'$ denote H or a methyl group,
$X_1$, $X_1'$, $X_2$, and $X_2'$ denote O, S, or $NR_\alpha$ [where $R_\alpha$ is H or a $C_{1-6}$ alkyl group],
m is an integer of 1 to 4,
n is an integer of 0 to 4,
k and k' are 0 or 1,
$R_a$ is a $C_{8-40}$ organic residue having a valence of (m+1), and
$R_a'$ is a $C_{1-40}$ organic residue having a valence of (n+1); and
(b) 0 to 199 parts by weight of a monomer which is copolymerizable with said compound (a).

Having now briefly described the invention, a more complete understanding of the invention can be obtained by reference to the description of the preferred embodiments which is provided herein for purposes of illustration only, and are not intended to be limiting unless otherwise specified.

DETAILED DESCRIPTION OF THE INVENTION

The adhesive of this invention is characterized by the fact that the above-mentioned compound (a) is used as a monomer that, on polymerization, exhibits adhesive properties for the hard tissues of the living body, metals, and ceramics. (This monomer may be referred to as the adhesive monomer hereinafter.)

The term "organic residue" as used herein comprises the following:
(i) a hydrocarbon group which may have an OH group, COOH group, $NH_2$ group, or halogen (F, Cl, Br, or I) as a substituent group, and
(ii) a group composed of a plurality (2 to 20) of hydrocarbon groups which may have the above-mentioned substituent group, said hydrocarbon groups being connected to one another through the linkage of the type of ether, thioether, ester, thioester, thiocarbonyl, amide, carbonyl, sulfonyl, urethane,

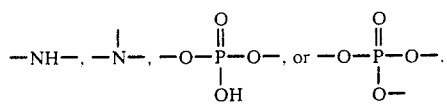

The organic group (ii) includes an organic residue in which the main chain is made up of a plurality of hydrocarbon groups and a part of the hydrocarbon groups constitutes the side chain of the skeleton.

Illustrated below are some of the hydrocarbon groups (represented by A) connected through the linkage (represented by (B) of

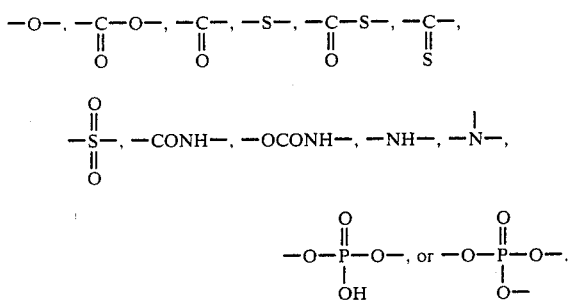

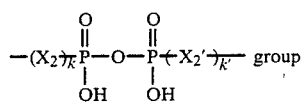

For simplicity, the group having the double bond is expressed by [C=C] and the

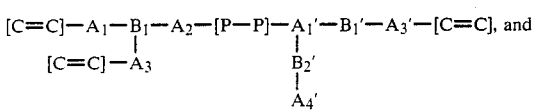

is expressed by [P—P].

[C=C]—$A_1$—[P—P]—$A_1$—[C=C],
[C=C]—$A_1$—[P—P]—$A_2$, [C=C]—$A_1$—$B_1$—$A_2$—$B_2$—$A_3$—[P—P]—$A_1'$—$B_1'$—$A_2'$—$B_2'$—$A_3$—[C=C],

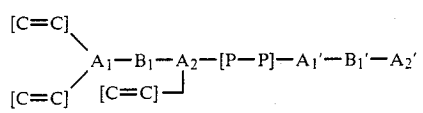

The term "hydrocarbon group" as used in this invention comprehends halogenated hydrocarbon groups, unless otherwise noted.

Among the compounds of the above formula, a pyrophosphate derivative of (meth)acrylic ester in which $X_1$, $X_1'$, $X_2$, and $X_2'$ are oxygen and k and k' are 1 provides an adhesive which can be used in a variety of application areas. Particularly, those compounds in which $R_a = R_a'$, $R_1 = R_1'$, and m=n are easy to synthesize. Those compounds in which m=n=1 are preferable from the standpoint of adhesive strength. The preferred compound which exhibits high adhesive strength is one represented by formula (I) in which $R_a$ is (i) a $C_{8-30}$ hydrocarbon group which may be substituted with a halogen, hydroxyl group, amino group, or carboxyl group, or (ii) a $C_{8-30}$ hydrocarbon group in which 2 to 7 hydrocarbon groups, each of which may be substituted with a halogen, hydroxyl group, amino group, or carboxyl group and has 1 to 29 carbon atoms and at least one of them has 3 or more carbon atoms are connected to one another through a linkage of the type of ether, thioether, ester, thioester, thiocarbonyl, amide, carbonyl, sulfonyl, urethane,

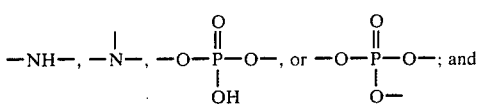

$R_a'$ is (i) a $C_{1-30}$ hydrocarbon group which may be substituted with a halogen, hydroxyl group, amino group, or carboxyl group, or (ii) a $C_{2-30}$ hydrocarbon group in which 2 to 7 hydrocarbon groups, each of which may be substituted with a halogen, hydroxyl group, amino group, or carboxyl group and has 1 to 29 carbon atoms are connected to one another through a linkage of the type of ether, thioether, ester, thioester, thiocarbonyl, amide, carbonyl, sulfonyl, urethane,

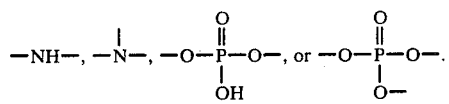

The particularly preferred structure of $R_a$ is:

(i) $-(CH_2)_i-$ [where i is a natural number from 8 to 20.]

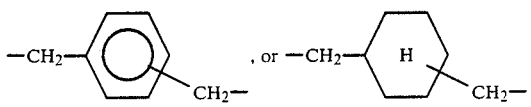

(ii)

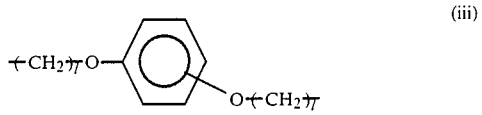

(iii)

[where l is 2, 3, or 4.]

(iv)

[where p is 0 or 1, and $R_6$ is a $C_{5-16}$ hydrocarbon group.]

Examples of the adhesive monomer used in this invention are illustrated below.

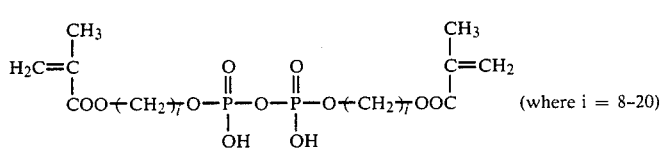

(where i = 8-20)

-continued
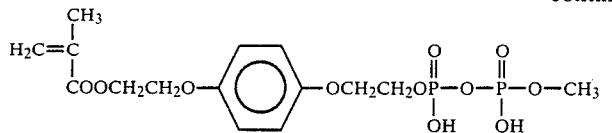
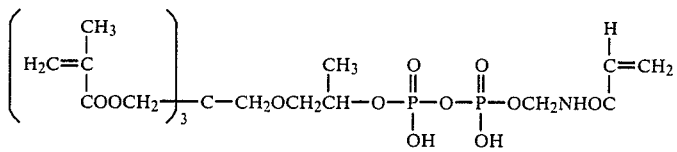
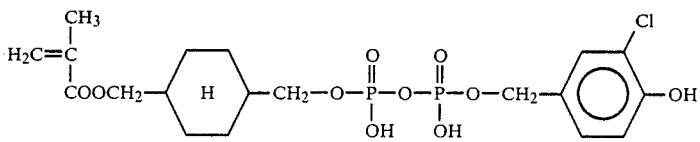
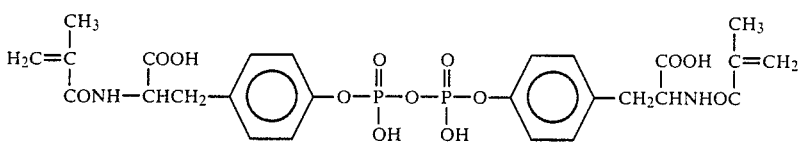
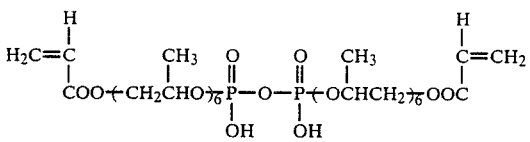
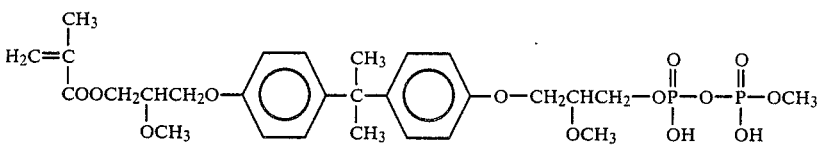
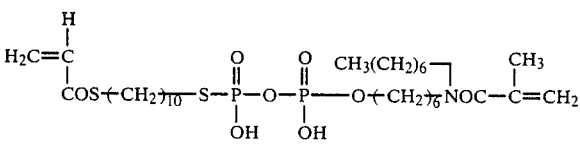
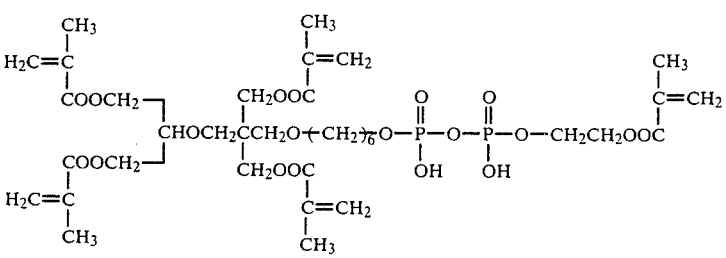
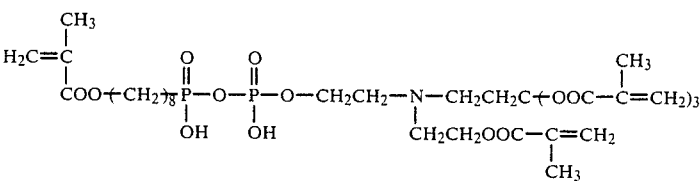
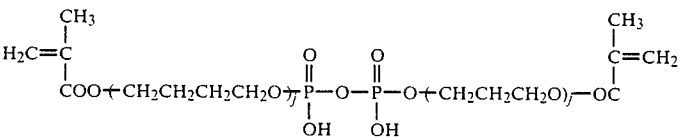
(where J = 2-10)

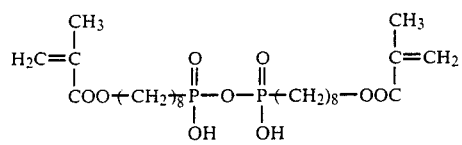
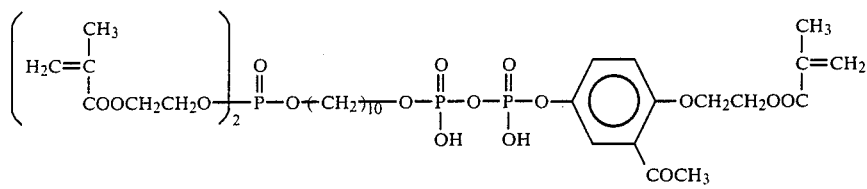
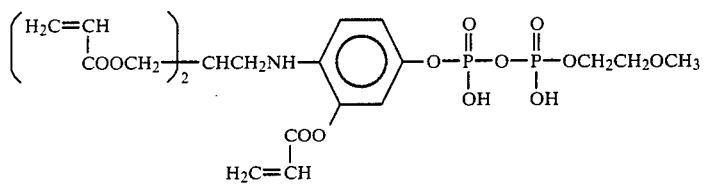
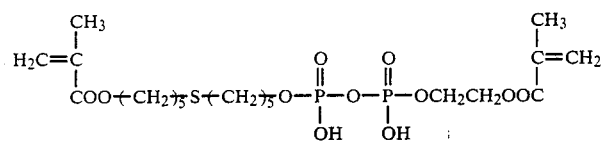
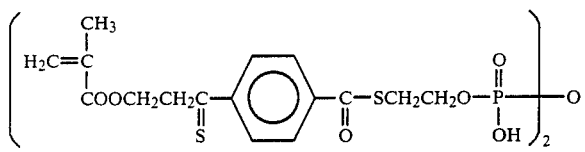
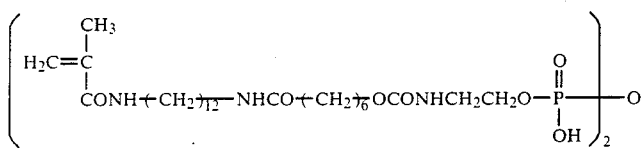
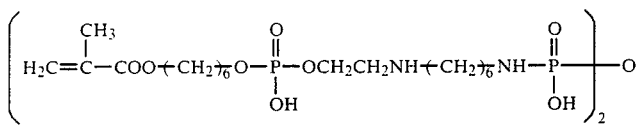
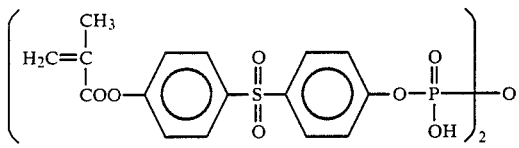
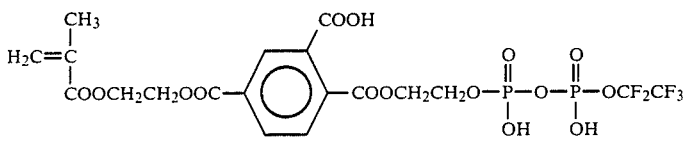

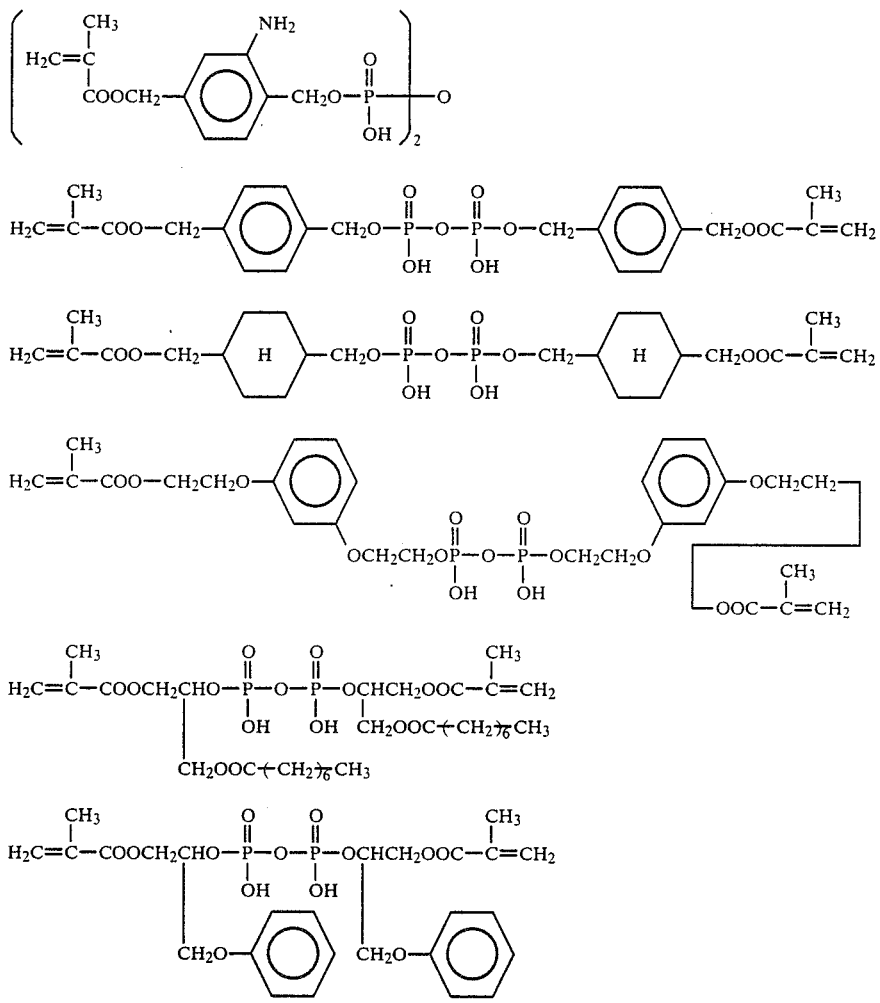

In the case where $R_a$ in the compound of formula (I) has a carbon number of 7 or less, the resulting adhesive is extremely poor in adhesion to teeth, metallic materials, and ceramic materials and is also poor in terms of the water resistance of its adhesive strength, as compared with the adhesive of this invention. In general, there is a tendency that as the carbon number of $R_a$ increases, the resulting adhesive increases and then decreases in adhesive strength. When $R_a$ has the carbon number 8 to 40, preferably 8 to 30, sufficient adhesive strength is obtained to achieve the object of this invention. $R_a'$ has no lower limit with respect to carbon number; but when it has a carbon number in excess of 40, the resulting adhesive is poor in adhesive strength.

The compound of formula (I) can be synthesized according to the process for synthesizing phosphorus-containing compounds described in the following literature.

Organophosphorus Compounds, by G. M. Kosolapoff, published by Wiley, 1950.

Organophosphorus Monomers and Polymers, by Ye. L. Gefter, published by Pergamon Press, 1962

Modern Organic Synthesis Series 5, Organic phosphorus compounds, edited by The Society of Synthetic Chemistry, Japan, published by Gihodo Bellstein (Springer-Verlarg)

For example, the compound of the formula (I) wherein $X_1$, $X_1'$, $X_2$, and $X_2'$ are oxygen; k and k' are 1; $R_a=R_a'$, $R_1=R_1'$, and m=n=1, or the compound of the following formula (II)

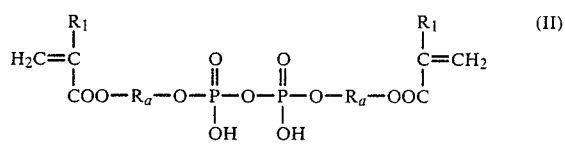

is synthesized as follows:

At first,

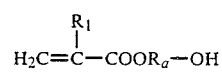

is synthesized through the esterification reaction of (meth)acrylic acid and HO—$R_a$—OH. The compound is changed into

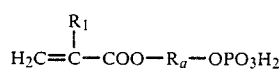

by esterifying the OH group with $POCl_3$ or pyrophosphoric acid. The phosphoric ester group is condensed by the dicyclohexylcarbodiimide process or by the dehydration with picryl chloride and pyridine. IF HO—$R_a$—OH is replaced by HS—$R_a$—SH, it is possible to synthesize a compound of formula (II) in which O may be replaced by S.

According to this invention, the adhesive (which may also be referred to as the adhesive composition) is prepared by mixing the compound of formula (I) with a vinyl monomer which is copolymerizable with the compound. The copolymerizable monomer affects the viscosity, wettability, curability, and mechanical properties of the adhesive. Thus it should be properly selected according to the intended use of the adhesive.

Usually, the copolymerizable monomer is meth(acrylate) type monomer, styrene type monomer, or vinyl acetate. The useful monomer are not limited to the above-disclosed list, but may also include (meth)acrylamide, N-n-butoxymethyl(meth)acrylamide, N-(hydroxymethyl)acrylamide, and other acrylamides; and (meth)acrylic acid, isobutylvinyl ether, diethyl fumarate, diethyl maleate, maleic anhydride, methyl vinyl ketone, allyl chloride, vinyl naphthalene, and vinylpyridine among others. The above-mentioned styrene type monomer includes those compounds (such as divinyl benzene and p-chlorostyrene) represented by $$CH_2=CH-\bigcirc \quad \text{or} \quad CH_2CH-\bigcirc-Q$$

(where Q denotes a halogen or a $C_{1-6}$ hydrocarbon group). The (meth)acrylate type monomer is one which is commonly used for anaerobic adhesives and dental adhesives. Some of the (meth)acrylate type monomers are a (meth)acrylate monomer represented by $$(CH_2=CH-COO)_{\overline{t}}U,$$

where $R_1$ denotes H or $CH_3$, U denotes a $C_{1-50}$ organic group, t denotes an integer of 1 to 4, and the organic group is defined above. Examples of such monomer include the following:

(i) Monofunctional (meth)acrylate

Methyl (meth)acrylate, ethyl (meth)acrylate, n-butyl (meth)acrylate, iso-butyl (meth)acrylate, n-hexyl (meth)acrylate, 2-ethylhexyl (meth)acrylate, benzyl (meth)acrylate, decyl (meth)acrylate, lauryl (meth)acrylate, stearyl (meth)acrylate, 2-hydroxyethyl (meth)acrylate (HEMA), 2-hydroxypropyl (meth)acrylate, dimethylaminoethyl (meth)acrylate, diethylaminoethyl (meth)acrylate, 3-chloro-2-hydroxypropyl methacrylate, and 2,3-dibromopropyl (meth)acrylate.

(ii) Difunctional (meth)acrylate (a) One in which U is —$CH_2CH_2(OCH_2CH_2)_s$— or $$-CH_2CH(OCH_2CH)_s-$$
$$\quad\ |\qquad\qquad |$$
$$\ CH_3\qquad\quad CH_3$$

(where s is an integer of 0 to 15)

Ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, and tripropylene glycol di(meth)acrylate.

(b) One in which U is an alkylene of carbon number 3 to 12

Propanediol di(meth)acrylate, glycerin di(meth)acrylate, 1,3-butanediol di(meth)acrylate, 1,4-butanediol di(meth)acrylate, 1,5-pentanediol di(meth)acrylate, 1,6-hexanediol di(meth)acrylate, neopentylglycol di(meth)acrylate, 1,10-decanediol di(meth)acrylate, and dibromoneopentyl glycol dimethacrylate.

(c) One in which U has a residue of bisphenol-A derivative

Bisphenol-A di(meth)acrylate, 2,2-bis[(meth)acryloyloxy polyethoxyphenyl]propane, $$[CH_2=\overset{R_1}{\underset{|}{C}}-COO(CH_2CH_2O)_t-\bigcirc-\overset{CH_3}{\underset{\underset{CH_3}{|}}{C}}-\bigcirc-(OCH_2CH_2)_t-O-OC-\overset{R_1}{\underset{|}{C}}=CH_2$$

where t is an integer of 1 to 9], 2,2'-bis(4-acryloyloxy propoxyphenyl)propane, and 2,2-bis[4-(3-methacryloyloxy-2-hydroxypropoxy)phenyl]propane (Bis-GMA). Preferable among them are those in which U has a carbon number 15 to 30.

(d) One in which U is $$\qquad\quad OH\qquad\qquad\qquad OH$$
$$\qquad\quad\ |\qquad\qquad\qquad\ \ |$$
$$-CH_2CHCH_2O(CH_2CH_2)_uOCH_2CHCH_2-$$

(where u is 1 or 2).

1,2-bis[3-(meth)acryloyloxy-2-hydroxypropoxy]ethane, and 1,4-bis[3-(meth)acryloyloxy-2-hydroxypropoxy]butane.

(e) One in which U is JOCONHTNHCOOJ, Urethane di(meth)acrylate, where J denotes a $C_{2-10}$ alkylene, and T denotes an organic diisocyanate residue of carbon number 1 to 50 as disclosed in Japanese Patent Laid-open No. 687/1975.

(iii) Tri- and tetrafunctional methacrylates

Trimethylolpropane tri(meth)acrylate, trimethylolethane tri(meth)acrylate, tetramethylolmethane tetra(meth)acrylate, and N,N'-(2,2,4-trimethylhexamethylene) bis[2-(aminocarboxy)propane-1,3-diol]tetramethacrylate.

The above-mentioned copolymerizable monomers may be used individually or in combination with one another. The most preferred of the above monomers as dental adhesive is methacrylate ester, and it should preferably account for more than 50 wt% of the total copolymerizable monomer. Preferred examples of methacrylate ester include methyl methacrylate, ethyl methacrylate, HEMA, n-hexyl methacrylate, benzyl methacrylate, lauryl methacrylate, bis-GMA, bisphenol-A dimethacrylate, 2,2-bis[(meth)acryloyloxy polyethoxyphenyl]propane, ethylene glycol dimethacrylate, diethylene glycol dimethacrylate, triethylene glycol dimethacrylate, 1,6-hexanediol dimethacrylate, 1,10-decanediol dimethacrylate, neopentyl glycol dimethacrylate, and trimethylolethane trimethacrylate.

In the adhesive of this invention, the compound of formula (I) should be contained more than 0.5 wt% in the total polymerizable monomer; in other words, the above-mentioned copolymerizable monomer should be used in an amount of 0 to 199 parts by weight for 1 part by weight of the compound of formula (I). If the content of the compound of formula (I) is less than 0.5 wt%, the resulting adhesive is insufficient in adhesive strength. The compound of formula (I) should preferably be used more than 1.5 wt%.

The adhesive of this invention exhibits its adhesive strength when polymerized and cured after application to the adherend or filling into the cavity. The curing is accomplished physically with heating or irradiation of X-rays, ultraviolet rays, or visible light, or chemically with a polymerization initiator. Usually, the adhesive is incorporated with a photosensitizer or a polymerization initiator to facilitate curing. The photosensitizers or polymerization initiators are collectively called a curing agent in this invention. The curing agent that can be used in this invention includes organic peroxides, azo compounds, organometallic compounds, redox initiators, and photosensitizers for ultraviolet rays and visible light. Examples of curing agents include benzoyl peroxide, di-t-butyl peroxide, cumene hydroperoxide, t-butylhydroperoxide, methyl ethyl ketone peroxide, azobisisobutyronitrile, tributyl borane, organic sulfinic acid (or salt thereof), hydrogen peroxide/$Fe^{2+}$ salt, cumene hydroperoxide/$Fe^{2+}$ salt, benzoyl peroxide/N,N-dialkylaniline derivative, ascorbic acid/$Cu^{2+}$ salt, organic sulfinic acid (or salt thereof)/amine (or salt thereof)/peroxide, α-diketone/allylthiourea (visible light curing), benzoin methyl ether, benzoinethyl ether, benzyl, diacetyl, diphenyldisulfide, and di-β-naphthyl sulfide. Preferable among them are benzoyl peroxide, azobisisobutyronitrile, tributyl borane, and organic sulfinic acid (or salt thereof)/diacyl peroxide/aromatic secondary or tertiary amine (or salt thereof). The aromatic sulfinic acid includes benzenesulfinic acid, p-toluenesulfinic acid, β-naphthalenesulfinic acid, and styrenesulfinic acid. The cation which forms a salt with the sulfinic acid is an alkali metal ion, alkaline earth metal ion, or ammonium ion. The former two are preferred from the standpoint of storage stability and adhesive strength. Examples of cations are $Li^+$, $Na^+$, $K^+$, $Mg^{2+}$, $Ca^{2+}$, and $Sr^{2+}$. The preferred examples of aromatic amines include N,N-dimethylaniline, N,N-dimethyl-p-toluidine, N,N-diethanolaniline, N,N-diethanol-p-toluidine, N-methylaniline, and N-methyl-p-toluidine. These amines may form a salt with hydrochloric acid, acetic acid, or phosphoric acid. The diacyl peroxide includes benzoyl peroxide, m-toluoylperoxide, 2,4-dichlorobenzoyl peroxide, octanoyl peroxide, lauroyl peroxide, and succinic acid peroxide. Preferable among them are benzoyl peroxide and m-toluoyl peroxide. These curing agents are added in an amount of 0.01 to 20 parts by weight, preferably 0.1 to 15 parts by weight, for 100 parts by weight of the polymerizable monomer.

In some cases, it is desirable to incorporate the adhesive of this invention with a volatile organic solvent having a boiling point lower than 150° C. at 760 Torr. Such an embodiment is preferable where the adhesive of this invention is used as a primer to be applied to the tooth cavity prior to the filling of a dental filling material. After application, the volatile organic solvent is vaporized by blowing air or nitrogen so that a film of the adhesive is formed on the adherend. The preferred organic solvent includes methanol, ethanol, acetone, methyl ethyl ketone, methyl acetate, ethyl acetate, dichloromethane, chloroform, ethyl ether, isopropyl ether, and toluene. The volatile organic solvent is used in an amount of less than 300 times (by weight), preferably less than 100 times, the weight of the total polymerizable monomer. Dilution in excess of 300 times results in a great decrease in adhesive strength due to an excessively thin film of polymerizable monomer formed after the volatilization of the solvent.

The adhesive of this invention may be incorporated with a known filler (inorganic, organic polymer, or inorganic-organic composite type). When incorporated with a filler, the adhesive of this invention can be used as a dental cement) for adhesion and filling), dental composite resin, and bone cement. The filler should be added in an amount of less than 1000 parts by wight, preferably 20 to 500 parts by weight, for 100 parts by weight of the polymerizable monomer. The filler improves the rheological properties of the adhesive composition at the time of its use, the mechanical properties of the cured adhesive, and the adhesive strength and the resistance of the adhesive strength to water. Examples of the inorganic filler include natural minerals such as quartz, felstone, pottery stone, wallastonite, mica, clay, kaolin, and marble; ceramics such as silica, alumina, silicon nitride, boron carbide, boron nitride, soda glass, barium glass, strontium glass, borosilicate glass, and lanthanum-containing glass ceramic; and water-insoluble inorganic salts such as barium sulfate and calcium carbonate. Usually, the inorganic filler undergoes surface treatment with a silane coupling agent such as γ-methacryloyloxypropyl trimethoxy silane, vinyl trimethoxy silane, vinyl triethoxy silane, vinyl trichlorosilane, vinyl tris(2-methoxyethoxy)silane, vinyl triacetoxy silane, and γ-mercaptopropyl trimethoxy silane. The organic polymeric filler includes polymethyl methacrylate, polyamide, polyester, polypeptide, polysulfone, polycarbonate, polystyrene, chloroprene rubber, nitrile rubber, styrene-butadiene rubber, and polyvinyl acetate. The inorganic-organic composite type filler includes the silane-treated inorganic filler coated with the above-mentioned polymer.

These fillers are used individually or in combination with one another. The filler may be formless, spherical, lamellar, or fibrous, having a particle diameter smaller than 100 microns. The polymeric filler may be dissolved in the polymerizable monomer or a volatile organic solvent. Inorganic fillers and inorganic-organic composite type fillers are preferable where the adhesive of this invention is used as a dental cement or dental composite resin, and organic fillers are preferable where it is used as a bone cement.

In the case where the adhesive of this invention is intended for industrial or home use, the adhesive may be incorporated with an organic solvent-soluble polymer such as PMMA, polystyrene, polyvinyl acetate, chloroprene rubber, butadiene rubber, nitrile rubber, and chlorosulfonated polyethylene in an amount of less than 200 parts by weight, preferably less than 120 parts by weight, for 100 parts by weight of the vinyl monomer composition, whereby the viscosity of the adhesive is increased, and the mechanical properties of the cured adhesive are improved.

In addition to the above-mentioned additives, the adhesive of this invention may be incorporated with a polymerization inhibitor, e.g., hydroquinone methyl ether(MEHQ), antioxidant, e.g., 2,6-di-tert-butyl-p-cresol (BHT), ultraviolet absorbing agent, pigment, phthalic acid diester, silicone oil, etc., as appropriate, according to the performance required. These additives are added in an amount of less than 10 parts by weight, preferably less than 5 parts by weight, for 100 parts by weight of the polymerizable monomers.

In the case where the adhesive of this invention is used in dentistry and orthopedics, a redox initiator of room temperature curing type is commonly used. In such a case, the oxidizing agent and the reducing agent should be packed separately to ensure storage stability, and a special attention should be paid to the package form. Examples of the package form include the two-pack systems, each pack containing vinyl compound plus reducing agent and vinyl compound plus oxidizing agent; vinyl compound plus oxidizing agent (or reducing agent) and volatile organic solvent plus reducing agent (or oxidizing agent); vinyl compound plus oxidizing agent (or reducing agent) and filler plus reducing agent (or oxidizing agent); or vinyl compound plus filler plus oxidizing agent and vinyl compound plus filler plus reducing agent. In the case of the three-component system composed of organic sulfinic acid (or salt thereof)/amine (or salt thereof)/peroxide, which is most suitable for the adhesive of this invention, the sulfinic acid and amine function as the reducing agent and the peroxide, as the oxidizing agent. In this case, a three-pack system may be employed in which the sulfinic acid and amine are separated from each other.

In the case where a photosensitizer is used as a curing agent, the package containing the vinyl compound and photosensitizer should be stored in a container shielded against light. In the case where an initiator such as tributyl borane is employed, which initiates polymerization in a short time on contact with the vinyl compound, the initiator and the vinyl compound should be packed separately from each other. The two-pack adhesive composition is mixed together immediately before use.

The adhesive of this invention exhibits outstanding adhesion for a variety of materials as enumerated below, and keeps the high adhesive strength under a wet condition over a long period of time.
(i) Hard tissues of the living body, such as teeth and bones.
(ii) Base metals and alloys thereof such as iron, nickel, chromium, cobalt, aluminum, copper, zinc, tin, stainless steel, and brass; and noble metal alloys containing 50 to 90% of gold or platinum, which are difficult to bond with a conventional adhesive.
(iii) Ceramics such as glass, porcelain, silica, and alumina.
(iv) Organic polymers such as polymethyl methacrylate, polyester, polyamide, polyurethane, polycarbonate, polysulfone, and polystyrene.

Because of its ability to exhibit high adhesive strength for a variety of materials as mentioned above, the adhesive of this invention will find use in various application areas. Examples of preferred applications are as follows:
(i) Dentistry The adhesive is applied to the wall of a tooth cavity to be filled with a composite resin which is usually composed of a polymerizable monomer, filler, and polymerization initiator. When supplied to the dentist, the adhesive is combined with the composite resin to form a system.

The adhesive composition incorporated with a filler is used as a composite resin to be filled in the tooth cavity. Not only does the adhesive composition function as a filling material but also it firmly adheres to the tooth.

The adhesive is used to bond an inlay, onlay, or abutment to a tooth cavity; to fasten a bridge, post, splint, or orthodontic bracket to teeth; or to bond a crown to an abutment.

The adhesive is used as a pit and fissure sealant.

For each application, the specific composition of the adhesive is selected as mentioned above. For example, if the adhesive is to be coated on a tooth prior to the filling of a composite resin, the adhesive composition may be prepared according to the recipe as shown in U.S. Pat. Nos. 4,259,075 and 4,259,117. That is, the adhesive composition is made up of 1.5 to 100 wt% of the above-mentioned vinyl compound (which exhibits adhesion on polymerization), a polymerizable monomer (such as bis-GMA, HEMA, and aliphatic dimethacrylate), an organic solvent (such as ethanol) as a diluent, and a curing agent of room temperature curing type. Also, if the adhesive composition is to be used in the form of a composite resin, it is prepared according to the recipe shown in the above-mentioned U.S. Patents. That is, the above-mentioned adhesive vinyl compound is added in an amount of 1.5 to 50 wt% (based on the total polymerizable monomers) to a conventional filling material composed of 20 to 40 wt% of polymerizable monomer (such as bis-GMA) and 80 to 60 wt% of filler.

The adhesive thus prepared is applied to a tooth in the usual way. On curing, the composite resin adheres to a tooth so firmly that it is not necessary to provide mechanical retention such as undercut. It is preferable to subject the tooth surface to acid etching before the adhesive of this invention is applied to the tooth; however, it provides practically sufficient adhesive strength without acid etching, unlike the compositions disclosed in U.S. Pat. Nos. 4,259,075 and 4,259,117. There is some fear for the injurious effect of acid etching on the dentin.

The adhesive composition to bond an inlay, onlay, or crown to a tooth cavity or abutment should preferably be composed of 1.5 to 50 parts by weight of the adhesive vinyl monomer, 98.5 to 50 parts by weight of the copolymerizable monomer, and 50 to 500 parts by weight of filler. With the adhesive composition thus prepared, it is possible to achieve the bonding of an inlay, onlay, or crown to a tooth cavity, which could not be achieved with a conventional luting cement.

In an additional application in the dentistry, a liquid composed of the adhesive vinyl monomer, copolymerizable monomer, and curing agent is applied to the tooth surface, followed by curing, so that the firmly-bonding film formed on the tooth surface prevents tooth decay.
(ii) Orthopedics The adhesive composition of this invention will find use as a bone cement to bond a ceramic or metallic artificial joint or splint to a bone. The adhesive composition for such use should preferably be composed of 90 to 98.5 parts by weight of methyl methacrylate, 10 to 1.5 parts by weight of adhesive vinyl monomer, and 50 to 150 parts by weight of polymethyl methacrylate.
(iii) General industrial and home uses Because of its outstanding adhesion to metals, ceramics, and organic polymers, the adhesive of this invention will find general use in the areas of transport, electric machines, building materials, can manufacture, ceramic industry, and home appliances. The present adhesive will also find use as coating materials such as a paint and an undercoating. When used for coating, it adheres much more firmly to the substrate than the existing adhesive of polymerization curing type (such as cyanoacrylate, epoxy resin, and second-generation acrylic adhesive), even if the substrate is stained with oil or wetted. This is a surprising feature of the adhesive of this invention.

Having generally described the invention, a more complete understanding can be obtained by reference to certain specific examples, which are intended for purpose of illustration only and are not intended to be limiting.

EXAMPLE 1

The adhesive monomer used in this invention was prepared as follows: A mixture of monomethacrylate ester and dimethacrylate ester of 1,12-docanediol was prepared by esterifying equimolar amounts of methacrylic acid and 1,12-dodecanediol at 90° C. in the presence of p-toluenesulfonic acid as a catalyst. After the determination of the molar ratio by high-speed liquid chromatography, the mixture was reacted at −50° C. with phosphorus oxychloride in an equimolar amount of the monoester. The remaining P-Cl bond was hydrolyzed at 0° C. to give a mixture of 12-methacryloxydodecyl dihydrogen phosphate and 1,12-dodecanediol dimethacrylate. After removal of dimethacrylate by extraction with n-hexane, there was obtained 12-methacryloyloxy dodecyldihydrogen phosphate. 35 g of this phosphate and 10.3 g of dicyclohexylcarbodiimide were dissolved in 100 cc of ethyl acetate, followed by stirring at room temperature for 5 hours. The crystals of urea derivative which had separated out were filtered off. After adding 15 mg of BHT to the filtrate, the solvent was distilled away from the filtrate under reduced pressure to yield 33 g of nonvolatile residue. By elemental analysis and $H^1$- and $P^{31}$-NMR analyses, it was confirmed that the residue is a pyrophosphate ester of the following formula.

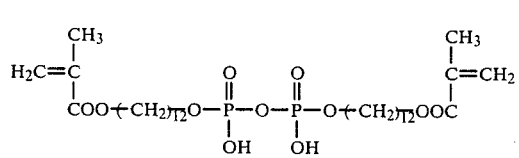

A two-pack type primer was prepared from this compound according to the following recipe.

|  | Parts by weight |
| --- | --- |
| Formulation 1. |  |
| Bis-GMA | 50 |
| HEMA | 43 |
| Compound (A) | 7 |
| Benzoyl peroxide | 2 |
| Formulation 2. |  |
| Ethanol | 100 |
| Sodium benezensulfinic acid | 3 |
| N,N—dimethyl-p-toluidine | 0.7 |

A specimen for adhesion was prepared by embedding a human molar in an epoxy resin in a cylindrical holder and then cutting the crown so that the dentin was exposed. On the other hand, a stainless steel rod, measuring 7 mm in diameter and 25 mm long was provided. The surface of the dentin and the end of the stainless steel rod were polished with #1000 sand paper. The polished surface of the dentin was covered with a piece of adhesive tape having a hole 5 mm in diameter. This hole establishes the area of adhesion. Formulation 1 and formulation 2 were mixed in equal quantities, and the mixture was applied to the dentin surface and the end of the stainless steel rod. Immediately, air was blown to the coated surface by using an air syringe to vaporize ethanol. A commercial dental composite "Clearfil-F" was mixed and the resulting paste was cast up on the end of the stainless steel rod. The stainless steel rod was pressed against the surface of the dentin, with the paste interposed between the two surfaces. After being kept pressed for 30 minutes, the dentin specimen and the stainless steel rod which had been bonded together were dipped in water at 37° C. for one day. Tensile bonding strength was measured. The bonding strength was 66 kg/cm² when failure occurred at the dentin-composite resin interface.

COMPARATIVE EXAMPLE 1

Example 1 was repeated except that the compound (A) was replaced by a known pyrophosphate ester of the following formula (B).

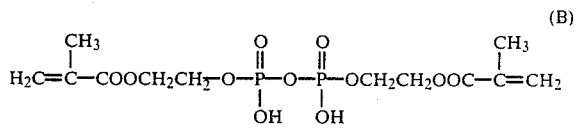

The tensile bonding strength was 8 kg/cm².

EXAMPLE 2

As the adherends, round rods measuring 7 mm in diameter and 25 mm long were prepared from iron, aluminum, copper, nickel, porcelain, α-alumina, glass, polymethyl methacrylate, and polycarbonate. The end of each rod was polished with #1000 silicon carbide sand paper. A 5% ethanol solution of compound (A) was sparingly applied to each adherend, followed by evaporation of ethanol by an air syringe. A powder-liquid type adhesive prepared by mixing the following formulations in equal quantities was applied to the primed adherend. Two rods of the same kind were butted together.

|  | Parts by weight |
| --- | --- |
| Formulation 3. |  |
| Methyl methacrylate | 100 |
| Benzoyl peroxide | 1 |
| Formulation 4. |  |
| Polymethyl methacrylate powder | 100 |
| Sodium benzenesulfinate powder | 3 |
| N,N—diethanol-p-toluidine | 1 |

After 1 hour, the bonded specimens were dipped in water at room temperature for 10 days. The tensile bonding strength was measured. The results are as follows:

| Iron | 351 kg/cm² |
| --- | --- |
| Aluminum | 298 kg/cm² |

| | |
|---|---|
| Copper | 266 kg/cm$^2$ |
| Nickel | 335 kg/cm$^2$ |
| Porcelain | 187 kg/cm$^2$ |
| α-Alumina | 172 kg/cm$^2$ |
| Glass | 81 kg/cm$^2$ |
| Polymethyl methacrylate | 153 kg/cm$^2$ |
| Polycarbonate | 108 kg/cm$^2$ |

COMPARATIVE EXAMPLE 2

Example 2 was repeated except that compound (A) was replaced by compound (B). The bonding strength for iron, alumina, copper, nickel, porcelain, α-alumina, and glass was lower than 50 kg/cm$^2$.

EXAMPLE 3

A powder-liquid type adhesive of the following composition was prepared from compound (A).

| | Parts by weight |
|---|---|
| Formulation 5. | |
| Bis-GMA | 40 |
| HEMA | 30 |
| Neopentylglycol dimethacrylate | 20 |
| Compound (A) | 10 |
| Benzoyl peroxide | 2 |
| MEHQ | trace amount |
| Formulation 6. | |
| Silane-treated quartz powder | 100 |
| Sodium benzenesulfinate powder | 0.3 |
| N,N—diethanol-p-toluidine | 0.4 |

An adherend specimen was prepared by embedding the crown of a bovine anterior tooth in an epoxy resin in a cylindrical holder, with the labial enamel surface exposed. After polishing with #1000 sand paper, the enamel surface underwent acid etching with 40% aqueous solution of orthophosphoric acid. After rinsing, the etched surface was dried by using an air syringe. On the other hand, there was provided a stainless steel round rod measuring 7 mm in diameter and 25 mm long, with the end polished with #1000 sand paper.

A pasty adhesive was prepared by mixing 0.1 g of formulation 5 and 0.3 g of formulation 6. The adhesive was applied to the end of the round stainless steel rod. The end of the rod was pressed against the etched surface. After being kept pressed for 1 hour, the specimens were dipped in water at 37° C. for 1 day. The tensile bonding strength was measured. The bonding strength was 205 kg/cm$^2$ when failure occurred at the enamel-adhesive interface.

EXAMPLES 4 TO 9

Adhesives were prepared from the compounds listed in Table 1 according to Example 1, and their bonding strength for human tooth dentin was evaluated. In addition, a powder-liquid type adhesive was prepared in the same way as in Example 3 except that compound (A) was replaced by the compounds in Table 1. Their bonding strength for an Ni—Cr alloy was evaluated.

A dental Ni—Cr alloy (Now Chrom (I), made by Towa Giken K.K.) was cast into a square plate measuring 4×10×10 mm. The 10×10 mm surface of the alloy plate was polished with #1000 sand paper. The polished surface was covered with a piece of adhesive tape having a hole 5 mm in diameter. This hole establishes the area of bonding. On the other hand, a stainless steel round rod measuring 7 mm in diameter and 30 mm long was provided. The end of the rod was polished by sandblasting with alumina abrasive having an average particle diameter of 33 microns at a pressure of 3.5 kg/cm$^2$. A paste obtained by mixing 0.3 g of adhesive powder and 0.1 g of adhesive liquid was applied to the end of the stainless steel round rod. The end of the stainless steel rod was pressed against the Ni—Cr alloy plate. After being kept pressed for 1 hour, the specimens were dipped in water at 37° C. for 1 day. The tensile bonding strength was measured on an Instron tensile tester, at a crosshead speed of 2 mm/min.

The results are shown in Table 1.

TABLE 1

| Example | Compound | Bonding strength (kg/cm$^2$) | |
|---|---|---|---|
| | | Human tooth | Ni—Cr alloy |
| 4 | $\left( H_2C=\underset{CH_3}{\overset{|}{C}}-COO-(CH_2)_{10}-O-\underset{OH}{\overset{O}{\overset{\|}{P}}}- \right)_2 O$ | 67 | 325 |
| 5 | $\left( H_2C=\underset{CH_3}{\overset{|}{C}}-COOCH_2-\bigcirc-CH_2O-\underset{OH}{\overset{O}{\overset{\|}{P}}}- \right)_2 O$ | 58 | 298 |
| 6 | $\left( H_2C=\underset{CH_3}{\overset{|}{C}}-COOCH_2-\langle H \rangle-CH_2O-\underset{OH}{\overset{O}{\overset{\|}{P}}}- \right)_2 O$ | 58 | 262 |

TABLE 1-continued

| Example | Compound | Bonding strength (kg/cm²) Human tooth | Bonding strength (kg/cm²) Ni—Cr alloy |
|---|---|---|---|
| 7 | $\left[H_2C=\overset{CH_3}{\underset{}{C}}-COOCH_2CH_2O-\underset{}{\bigcirc}-OCH_2CH_2O-\underset{OH}{\overset{O}{\underset{\|}{P}}}\right]_2-O$ | 64 | 320 |
| 8 | $\left[H_2C=\overset{CH_3}{\underset{}{C}}-COOCH_2\underset{CH_2OOC+CH_2\overline{)_6}CH_3}{\underset{\|}{CH}}-O-\underset{OH}{\overset{O}{\underset{\|}{P}}}\right]_2-O$ | 52 | 233 |
| 9 | $\left[H_2C-\overset{CH_3}{\underset{}{C}}OOCH_2\underset{CH_2O-\bigcirc}{\underset{\|}{CH}}-O-\underset{OH}{\overset{O}{\underset{\|}{P}}}\right]_2-O$ | 54 | 306 |

COMPARATIVE EXAMPLE 3

Adhesives were prepared according to Examples 4 to 9 from a compound of formula (C).

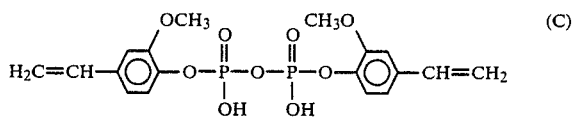

(C)

Their bonding strength for the human tooth dentin and an Ni—Cr alloy (Now Chrom (I), made by Towa Giken K.K.) was 11 kg/cm² and 33 kg/cm², respectively. These results are apparently inferior to those in Table 1.

EXAMPLE 10

A cylindrical cavity measuring 4 mm in diameter and 4 mm deep was formed on the lingual surface of a human molar by using a diamond bur. The cavity was dried by using an air syringe. A mixture of equal quantities of formulation 1 and formulation 2 in Example 1 was applied to the entire cavity wall. Air was blown to the coated surface by using an air syringe to vaporize ethanol. A commercial dental composite resin "Clearfil-F" was filled in the cavity in the usual way. The tooth specimen was dipped in water at 37° C. for 1 day. Then, the tooth specimen was dipped in water at 4° C. and water at 60° C. alternately 100 times for 1 minute each. The water was colored with a dye. The tooth specimen was cut with a cutter to see if the dye had infiltrated into the interface between the tooth and the filler. The infiltration of the dye was not found at all.

EXAMPLE 11

A conical cavity measuring 6 mm in diameter and 4 mm deep was formed on the occlusal surface of a human molar. An inlay that fits in the cavity was cast from type III gold alloy. A 1:3.0 mixture (by weight) of formulation 5 and formulation 6 in Example 3 was applied to the conical surface of the inlay. The inlay was forced into the cavity to effect bonding. After 30 minutes, the tooth specimen was dipped in water at 37° C. for 1 day. Then, the tooth specimen was subjected to thermal cycling test by dipping in water at 4° C. and water at 60° C. alternately 100 times. After the test, the inlay stayed in the cavity so firmly that it could not be pried off by a knife tip.

EXAMPLE 12

A 1-mm thick plate that fits to the lingual surface of a human anterior tooth was prepared by casting from an Ni—Cr alloy (Ni: 76%, Cr: 12%, Mo: 3%, others: 9%). The surface of the casting that comes into contact with the tooth was polished by sandblasting with 33-micron alumina abrasive. The lingual surface of the anterior tooth underwent acid etching for 1 minute with 40% aqueous solution of phosphoric acid.

A 1:3.0 mixture by weight of formulation 5 and formulation 6 in Example 3 was applied to the surface of the casting. The casting was bonded to the lingual surface of the anterior tooth. After 10 minutes, the bonded specimens were dipped in water at 37° C. for 1 day. The tensile bonding strength was 183 kg/cm². Interfacial failure occurred at the tooth surface.

EXAMPLE 13

A pit and fissure sealant for filling the fissure of a molar was prepared according to the following composition.

|  | Parts by weight |
|---|---|
| Formulation 7. |  |
| 2,2-Bis(methacryloyloxypoly-ethoxyphenyl)propane | 60 |
| Neopentylglycol dimethacrylate | 20 |
| Compound (A) | 10 |
| HEMA | 10 |
| Benzoyl peroxide | 2 |
| Formulation 8. |  |

| | Parts by weight |
|---|---|
| Bis-GMA | 40 |
| HEMA | 40 |
| Neopentylglycol dimethacrylate | 20 |
| Sodium benzenesulfinate | 2 |
| N,N—diethanol-p-toluidine | 2 |

The fissure of a human molar was cleaned with an explorer, followed by washing and drying. The sealant (a 1:1 mixture of formulation 7 and formulation 8) was filled in the fissure without etching. Ten minutes after curing, the tooth specimen was dipped in water at 37° C. for 1 day. Then, the tooth specimen was dipped in water at 4° C. and water at 60° C. alternately 100 times for 1 minute each. The water was colored with a dye. The tooth specimen was cut with a cutter to see if the dye had infiltrated into the interface between the tooth and the filling material. The infiltration of the dye was hardly found.

EXAMPLE 14

A cylindrical cavity measuring 4 mm in diameter and 4 mm deep was formed on the buccal surface of a human molar by using a diamond bur. The cavity wall underwent acid etching for 1 minute with 40% aqueous solution of phosphoric acid, followed by washing and drying. The paste obtained by mixing formulation 5 and formulation 6 in Example 3 in the ratio of 1:3.0 by weight was filled in the cavity. Ten minutes after curing, the tooth specimen was dipped in water at 37° C. for 1 day. Then, the heat-cycle test was conducted as in Example 13. The infiltration of dye into the interface was hardly found.

Having now fully described the invention, it will be apparent to one of ordinary skill in the art that many changes and modifications can be made thereto, without departing from the spirit or scope of the invention as set forth therein.

What is claimed as new and desired to be secured by Letters Patent of the United States is:

1. An adhesive which comprises
   (a) 1 part by weight of a compound of the formula

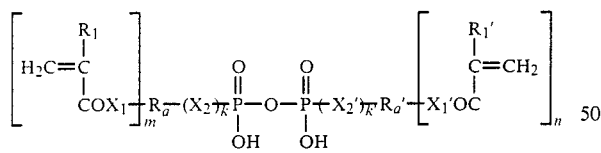

wherein
   $R_1$ and $R_1'$ are H or a methyl group,
   $X_1$, $X_1'$, $X_2$, and $X_2'$ are O, S, or $NR_\alpha$;
   wherein
   $R_\alpha$ is H or a $C_{1-6}$ alkyl group,
   m is an integer of 1 to 4,
   n is an integer of 0 to 4,
   k and k' are 0 or 1,
   $R_a$ is a $C_{8-40}$ organic residue having a valence of (m+1), and
   $R_a'$ is a $C_{1-40}$ organic residue having a valence of (n+1); and
   (b) 0 to 199 parts by weight of a monomer which is copolymerizable with the compound of (a).

2. The adhesive as set forth in claim 1, wherein $X_1$, $X_1'$, $X_2$, and $X_2'$ are oxygen, and k and k' are 1.

3. The adhesive as set forth in claims 1 and 2, wherein $R_a'$ is $R_a$, $R_1'$ is $R_1$, and n is equal to m.

4. The adhesive as set forth in claim 3, wherein m and n are 1.

5. The adhesive as set forth in claim 4, wherein $R_a$ is $-(CH_2)-_n$; wherein n is 8 to 20.

6. The adhesive as set forth in claim 4, wherein the $R_a$ is

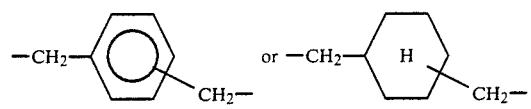

7. The adhesive as set forth in claim 4, wherein $R_a$ is

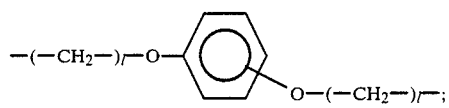

wherein l is 2, 3, or 4.

8. The adhesive as set forth in claim 4, wherein $R_a$ is

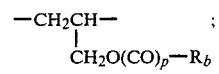

wherein p is 0 or 1, and $R_b$ is a $C_5$-$C_{16}$ hydrocarbon group.

9. The adhesive as set forth in claim 1, wherein $R_a$ is a $C_{8-30}$ first hydrocarbon residue or $C_{8-30}$ first hydrocarbon residue substituted with a halogen, hydroxyl, amino or carboxyl group; said first hydrocarbon residue being formed by 2 to 7 $C_1$-$C_{29}$ hydrocarbon residues and at least one of them having 3 or more carbon atoms, said forming first hydrocarbon residues being connected to one another through a linkage group selected from the group consisting of ether, thioether, ester, thioester, thiocarbonyl, amide, carbonyl, sulfonyl, urethane, —NH—,

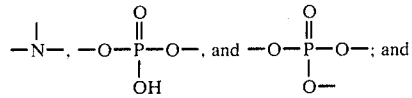

$R_a'$ is a $C_{2-30}$ second hydrocarbon residue or a $C_{2-30}$ second hydrocarbon residue substituted with a halogen, hydroxyl, amino or carboxyl group; said second hydrocarbon residue being formed by 2 to 7 $C_1$-$C_{29}$ hydrocarbon residues, said second forming hydrocarbon residues being connected to one another through a linkage group selected from the group consisting of ether, thioether, ester, thioester, thiocarbonyl, amide, carbonyl, sulfonyl, urethane, —NH—,

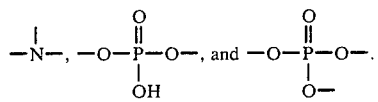

10. The adhesive of claim 9, wherein
$R_a'$ is a $C_{1-30}$ hydrocarbon residue which may be further substituted with a halogen, hydroxyl, amino or carboxyl group.

11. The adhesive of claim 9, wherein
$R_a$ is a $C_{8-30}$ hydrocarbon group which may be further substituted with a halogen, hydroxyl, amino or carboxyl group.

12. The adhesive as set forth in claim 1, further comprising a curing agent in an amount of 0.01 to 20 parts by weight per 100 parts by weight of the polymerizable monomers (a)+(b).

13. The adhesive as set forth in claim 12, wherein the curing agent is a redox type polymerization initiator.

14. The adhesive as set forth in claim 12, wherein the curing agent is a photosensitizer.

15. The adhesive as set forth in claim 1, further comprising a volatile organic solvent having a boiling point lower than 150° C. at 760 Torr in an amount of less than 300 times by weight of the polymerizable monomers (a)+(b).

16. The adhesive as set forth in claim 1, further comprising a filler in an amount of 20 to 500 parts by weight for 100 parts by weight of the polymerizable monomers (a)+(b).

17. The adhesive as set forth in claim 1, wherein the vinyl monomer (b) is selected from a methacrylate ester monomer, styrene monomer, and vinyl acetate.

18. The adhesive of claim 1, wherein
$R_a$ is a $C_{8-30}$ hydrocarbon residue or a $C_{8-30}$ hydrocarbon residue substituted with a halogen, hydroxyl, amino or carboxyl group, and
$R_a'$ is a $C_{1-30}$ hydrocarbon residue or a $C_{1-30}$ hydrocarbon residue substituted with a halogen, hydroxyl, amino or carboxyl group.

19. A method for restoring a decayed tooth which comprises:
(I) applying an adhesive to the surface of the tooth cavity; said adhesive comprising
(a) 1 part by weight of a compound of the formula

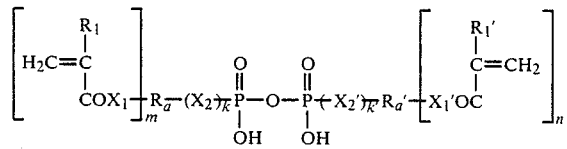

wherein
$R_1$ and $R_1'$ are H or a methyl group,
$X_1$, $X_1'$, $X_2$, and $X_2'$ are O, S, or $NR\alpha$;
wherein
$R_\alpha$ is H or a $C_{1-6}$ alkyl group,
m is an integer of 1 to 4,
n is an integer of 0 to 4,
k and k' are 0 or 1,
$R_a$ is a $C_{8-40}$ organic residue having a valence of (m+1), and
$R_a'$ is a $C_{1-40}$ organic residue having a valence of (n+1),
(b) 0 to 199 parts by weight of a monomer which is copolymerizable with said compound (a), and
(c) 0.01 to 20 parts by weight of a curing agent per 100 parts by weight of the polymerizable monomers of (a)+(b), and (II) subsequently filling the cavity with a dental filling material comprising a polymerizable monomer, a filler, and a curing agent.

20. The method as set forth in claim 19, wherein the adhesive further comprises a volatile organic solvent having a boiling point lower than 150° C. at 760 Torr in an amount of less than 300 times by weight per weight of the polymerizable monomers (a)+(b).

21. A method for restoring a decayed tooth which comprises filling an adhesive in the tooth cavity; said adhesive comprising
(a) 1 part by weight of a compound of the formula

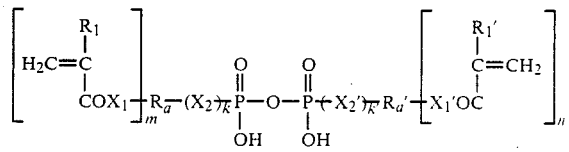

wherein
$R_1$ and $R_1'$ are H or a methyl group,
$X_1$, $X_1'$, $X_2$, and $X_2'$ are O, S, or $NR\alpha$;
wherein
$R_\alpha$ is H or a $C_{1-6}$ alkyl group,
m is an integer of 1 to 4,
n is an integer of 0 to 4,
k and k' are 0 or 1,
$R_a$ is a $C_{8-40}$ organic residue having a valence of (m+1), and
$R_a'$ is a $C_{1-40}$ organic residue having a valence of (n+1),
(b) 0 to 199 parts by weight of a monomer which is copolymerizable with said compound of (a),
(c) 20 to 500 parts by weight of filler per 100 parts by weight of the polymerizable monomers of (a)+(b), and
(d) 0.01 to 20 parts by weight of a curing agent per 100 parts by weight of the polymerizable monomers of (a)+(b).

22. A method of dental treatment which comprises bonding a dental restorative material to teeth or bonding dental restorative materials to each other with an adhesive comprising
(a) 1 part by weight of a compound of the formula

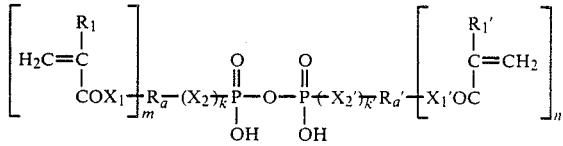

wherein
$R_1$ and $R_1'$ are H or a methyl group,
$X_1$, $X_1'$, $X_2$, and $X_2'$ are O, S, or $NR\alpha$; wherein $R\alpha$ is H or a $C_{1-6}$ alkyl group,
m is an integer of 1 to 4,
n is an integer of 0 to 4,
k and k' are 0 or 1,
$R_a$ is a $C_{8-40}$ organic residue having a valence of (m+1), and
$R_a'$ is a $C_{1-40}$ organic residue having a valence of (n+1),
(b) 0 to 199 parts by weight of a monomer which is copolymerizable with said compound of (a), (c) 20 to 500 parts by weight of filler per 100 parts by weight of the polymerizable monomers of (a)+(b), and (d) 0.01 to 20 parts by weight of a curing agent per 100 parts by weight of the polymerizable monomers of (a)+(b).

23. A method for preventing tooth decay which comprises coating a tooth surface with a composition which adheres to the tooth, said composition comprising (a) 1 part by weight of a compound of the formula

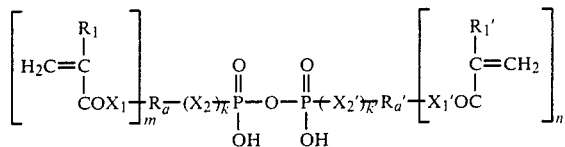

wherein
$R_1$ and $R_1'$ are H or a methyl group,
$X_1$, $X_1'$, $X_2$, and $X_2'$ are O, S, or $NR\alpha$;
wherein
$R\alpha$ is H or a $C_{1-6}$ alkyl group,
m is an integer of 1 to 4,
n is an integer of 0 to 4,
k and k' are 0 or 1,
$R_a$ is a $C_{8-40}$ organic residue having a valence of (m+1), and
$R_a'$ is a $C_{1-40}$ organic residue having a valence of (n+1), (b) 0 to 199 parts by weight of a monomer which is copolymerizable with said compound (a), and (c) 0.01 to 20 parts by weight of curing agent per 100 parts by weight of the polymerizable monomers of (a)+(b).

* * * * *

UNITED STATES PATENT AND TRADEMARK OFFICE
CERTIFICATE OF CORRECTION

PATENT NO. : 4,525,493
DATED : June 25, 1985
INVENTOR(S) : Ikuo Omura et al

It is certified that error appears in the above-identified patent and that said Letters Patent is hereby corrected as shown below:

At Column 6, line 56, delete "$R_6$", and insert therefor -- $R_b$ --.

At Column 7, last line, delete "J" and insert therefor -- j --.

At Column 11, line 66, delete "Bellstein" and insert therefor -- Beilstein --.

At Column 13, line 2, delete "IF" and insert therefor -- If --.

At Column 13, line 40, right-hand structure, delete "$CH_2CH$" and insert therefor -- $CH_2=CH$ --.

At Column 16, line 18, delete ") for" and insert therefor -- (for --.

At Column 27, line 1, delete "9" and insert therefor -- 1 --.

Signed and Sealed this

Seventh Day of January 1986

[SEAL]

Attest:

Attesting Officer

DONALD J. QUIGG

Commissioner of Patents and Trademarks